(12) United States Patent
Miyata et al.

(10) Patent No.: US 9,024,400 B2
(45) Date of Patent: May 5, 2015

(54) PHOTOELECTRIC CONVERSION ELEMENT, METHOD OF MANUFACTURING PHOTOELECTRIC CONVERSION ELEMENT, AND ELECTRONIC DEVICE

(71) Applicant: Seiko Epson Corporation, Tokyo (JP)

(72) Inventors: Takashi Miyata, Nagano (JP); Yasunori Hattori, Nagano (JP)

(73) Assignee: Seiko Epson Corporation, Tokyo (JP)

( * ) Notice: Subject to any disclaimer, the term of this patent is extended or adjusted under 35 U.S.C. 154(b) by 5 days.

(21) Appl. No.: 14/028,940

(22) Filed: Sep. 17, 2013

(65) Prior Publication Data

US 2014/0077321 A1    Mar. 20, 2014

(30) Foreign Application Priority Data

Sep. 20, 2012 (JP) ................. 2012-206654

(51) Int. Cl.
| | |
|---|---|
| *H01L 27/14* | (2006.01) |
| *H01L 31/0248* | (2006.01) |
| *H01L 31/18* | (2006.01) |
| *H01L 31/0216* | (2014.01) |
| *H01L 31/0224* | (2006.01) |

(Continued)

(52) U.S. Cl.
CPC ............ *H01L 31/0248* (2013.01); *H01L 31/18* (2013.01); *H01L 31/0216* (2013.01); *H01L 31/0224* (2013.01); *H01L 31/032* (2013.01); *H01L 31/09* (2013.01)

(58) Field of Classification Search
CPC ... H01L 27/30; H01L 27/3239; H01L 31/143; H01L 31/162; H01L 33/08; H01L 33/18; H01L 33/24; H01L 51/5032; H01L 25/048; H01L 27/288; H01L 27/32

USPC .......... 257/13, 79–103, 918, 40, 642–643, 257/759, E51.018–E51.022, E33.054, 257/E25.028, E25.032, E31.058, E31.063, 257/E31.115, E27.133–E27.139; 438/22–47, 69, 493, 503, 507, 956; 349/149–164

See application file for complete search history.

(56) References Cited

U.S. PATENT DOCUMENTS

| | | | | |
|---|---|---|---|---|
| 5,591,963 | A | * | 1/1997 | Takeda et al. ............... 250/214.1 |
| 8,415,557 | B2 |   | 4/2013 | Fukunaga et al. |

(Continued)

FOREIGN PATENT DOCUMENTS

| | | |
|---|---|---|
| JP | 2006-165386 A | 6/2006 |
| JP | 2007-123721 A | 5/2007 |

(Continued)

*Primary Examiner* — Selim Ahmed
*Assistant Examiner* — Moin Rahman
(74) *Attorney, Agent, or Firm* — Global IP Counselors, LLP (57) ABSTRACT

A method of manufacturing a photoelectric conversion element, which is provided with a substrate, a first electrode film having first and second conductive films provided on the substrate, a metal compound film covering the first electrode film, a semiconductor film connected with the metal compound film, a second electrode film connected with the semiconductor film, and an insulating film covering and surrounding the substrate, the first electrode film, the semiconductor film, and the metal compound film, the method including: forming the first conductive film to be connected with the substrate and the second conductive film to be connected with the first electrode film; forming the second conductive film in a predetermined shape using wet etching after the forming of the first and second conductive films, and forming the metal compound film which covers the first electrode film after the forming of the metal compound film.

4 Claims, 7 Drawing Sheets

(51) Int. Cl.
*H01L 31/032* (2006.01)
*H01L 31/09* (2006.01)

(56) References Cited

U.S. PATENT DOCUMENTS

2008/0271781 A1 11/2008 Kushiya et al.
2009/0217969 A1 9/2009 Matsushima et al.
2010/0236606 A1 9/2010 Kobayashi et al.

FOREIGN PATENT DOCUMENTS

| JP | 2010-212336 A | 9/2010 |
| JP | 2010-212337 A | 9/2010 |
| JP | 2010-239129 A | 10/2010 |

* cited by examiner

PHOTOELECTRIC CONVERSION ELEMENT, METHOD OF MANUFACTURING PHOTOELECTRIC CONVERSION ELEMENT, AND ELECTRONIC DEVICE

CROSS-REFERENCE TO RELATED APPLICATIONS

This application claims priority to Japanese Patent Application No. 2012-206654 filed on Sep. 20, 2012. The entire disclosure of Japanese Patent Application No. 2012-206654 is hereby incorporated herein by reference.

BACKGROUND

1. Technical Field

The present invention relates to a photoelectric conversion element, a method of manufacturing a photoelectric conversion element, and an electronic device.

2. Related Art

So-called CIS thin films which include copper (Cu), indium (In), and selenium (Se) and so-called CIGS thin films which include copper (Cu), indium (In), gallium (Ga), selenium (Se), and the like are known as thin films which form semiconductor devices which have a chalcopyrite structure. The CIS and CIGS thin films are frequently used in solar batteries since the photoelectric conversion rate is excellent. In addition, application of the CIS and CIGS thin films to sensors and the like as photoelectric conversion elements is desired in order to have a high light sensitivity over a wide wavelength range from visible light to near-infrared light.

For example, Japanese Unexamined Patent Application Publication No. 2007-123721 (FIG. 2) discloses a photoelectric conversion element which has a p type compound semiconductor thin film with a chalcopyrite structure which functions as a light absorbing layer by being laminated on an electrode film which is provided on a substrate.

SUMMARY

However, in a step where a semiconductor thin film with a chalcopyrite structure is patterned, there is a risk that the electrode film which is the lower layer may be damaged in a case where a dry etching method is used in order to remove portions of the semiconductor thin film which are not necessary. In addition, when the etching amount is controlled (suppressed) in order to suppress damage to the electrode film due to the dry etching, there is a risk that productivity may be decreased since residue from the electrode film occurs due to the dry etching and it is necessary to remove the residue using a wet etching method or the like.

The present invention was carried out in order to solve at least a portion of the problems described above and it is possible to realize the present invention as the following forms or aspects.

A method of manufacturing a photoelectric conversion element according to the present aspect, which is provided with a substrate, a first electrode film which has a first conductive film and a second conductive film which are provided on the substrate, a metal compound film which is provided to cover the first electrode film, a semiconductor film which is provided to be connected with the metal compound film, a second electrode film which is provided to be connected with the semiconductor film, and an insulating film which is provided to cover and surround the substrate, the first electrode film, the semiconductor film, and the metal compound film, is a method which includes forming the first conductive film to be connected with the substrate and the second conductive film to be connected with the first electrode film, forming the second conductive film in a predetermined shape using wet etching after the forming of the first conductive film and the second conductive film, and forming the metal compound film which covers the first electrode film after the forming of the second conductive film.

It is preferable that the method of manufacturing the photoelectric conversion element according to the aspect described above include forming the semiconductor film to be connected with the metal compound film, forming the metal compound film and the semiconductor film in a predetermined shape, forming the insulating film, and removing a portion of the insulating film and forming the second electrode film to be connected with the semiconductor film.

According to the method of manufacturing the photoelectric conversion element, the forming of the first conductive film and the second conductive film which is formed to connect to the first conductive film in the predetermined shape using wet etching is performed prior to the forming of the metal compound film. It is possible to apply an etchant where the etching rate is slower with regard to the first conductive film and faster with regard to the second conductive film in the wet etching which is performed in the forming of the first conductive film and the second conductive film. Due to this, it is possible to selectively pattern (etch) the second conductive film using wet etching and it is possible to suppress the etching residue of the second conductive film which occurs on the first conductive film and to suppress corrosion of the first conductive film and the substrate.

A photoelectric conversion element according to the present aspect is provided with a substrate, and a photoelectric conversion section which has a first electrode section and a second electrode section which are provided on the substrate and, and a light absorbing section, where the first electrode section has a first conductive film which has a first surface and a second surface, which is in a front and back relationship with the first surface, and is provided to be connected with the substrate and the first surface, and a second conductive film which is connected with the second surface and provided at the inner side of a peripheral edge of the first conductive film, the light absorbing section has a metal compound film which covers the second conductive film and is provided to be connected with the second surface, a semiconductor film which is provided to be connected with the metal compound film, and an insulating film which is connected with the substrate, surrounds the first conductive film, the metal compound film, and the semiconductor film, and is provided to expose the semiconductor film by a portion of the insulating film being opened, and the second electrode section has a second electrode film which is provided on the insulating film to be connected with the semiconductor film which is exposed from the insulating film.

According to the photoelectric conversion element, the second conductive film is provided on the second surface of the first conductive film so as to be surrounded by the first conductive film and the metal compound film. Due to this, it is possible to suppress a current which is converted by the light absorbing section which includes the metal compound film from leaking out from the second conductive film which is connected with the metal compound film to the insulating film. In addition, it is possible to suppress film peeling of the first conductive film, the metal compound film, and the insulating film which occurs due to the difference in the thermal expansion coefficients (the linear expansion coefficients) between the first conductive film, and the metal compound film and the insulating film.

It is preferable that the metal compound film in the photoelectric conversion element according to the aspect described above include copper (Cu), indium (In), and selenium (Se).

According to the photoelectric conversion element, it is possible to obtain a photoelectric conversion element with high photoelectric conversion efficiency by the metal compound film being a so-called CIS thin film with p type characteristics which includes copper, indium, and selenium compared to a case where the metal compound film is a silicon thin film.

It is preferable that the insulating film in the photoelectric conversion element according to the aspect described above include silicon oxide.

According to the photoelectric conversion element, by including silicon oxide in the insulating film, it is possible to have excellent adhesion between the substrate, the first conductive film, the second conductive film, the metal compound film, and the semiconductor film which are in contact with the insulating film and to suppress the film peeling between each of the films.

An electronic device according to the present aspect is mounted with the photoelectric conversion element described above.

By applying the photoelectric conversion element described above to the electronic device, it is possible to realize an improvement in the reliability of the electronic device which is mounted with the photoelectric conversion element.

BRIEF DESCRIPTION OF THE DRAWINGS

Referring now to the attached drawings which form a part of this original disclosure.

DETAILED DESCRIPTION OF EXEMPLARY EMBODIMENTS

Below, embodiments of the present invention will be described based on the diagrams. Here, in each of the diagrams which are illustrated below, since each of the constituent components is set to a size which is able to be recognized in the diagrams, there are cases in the description where the dimensions and proportions of each of the constituent components are appropriately varied from the actual constituent components.

First Embodiment

A photoelectric conversion element and a method of manufacturing a photoelectric conversion element according to the first embodiment will be described using FIG. 1 to FIG. 5.

Figure 1A:
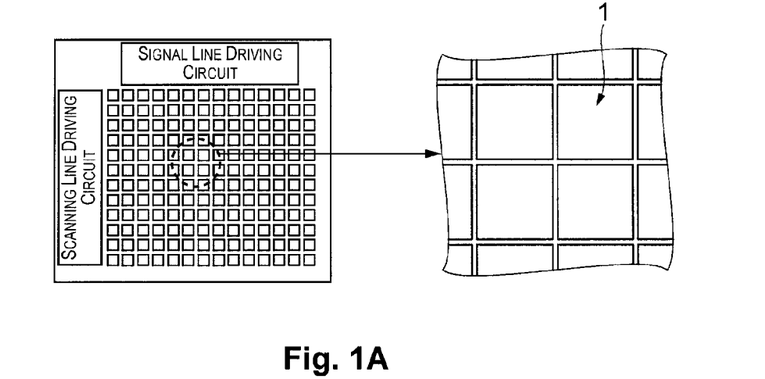
FIGS. 1A and 1B are diagrams schematically illustrating a schematic configuration of a photoelectric conversion element according to a first embodiment.
Figure 1B:
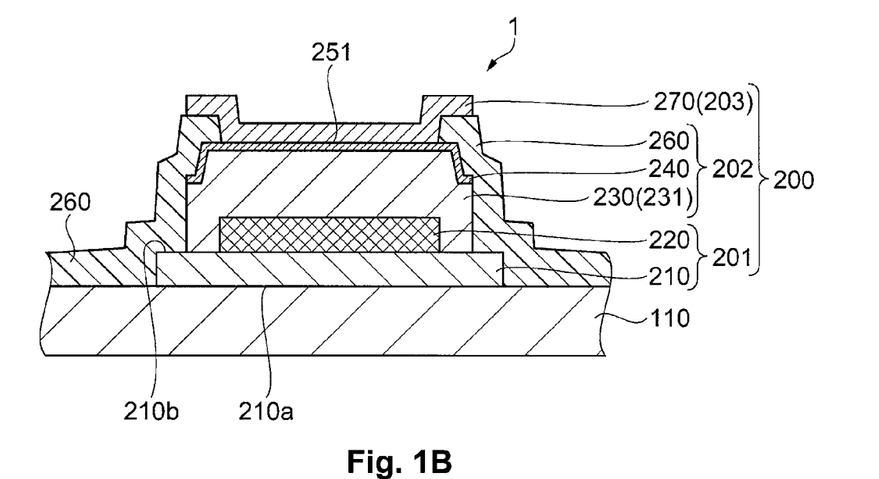
Figure 2:
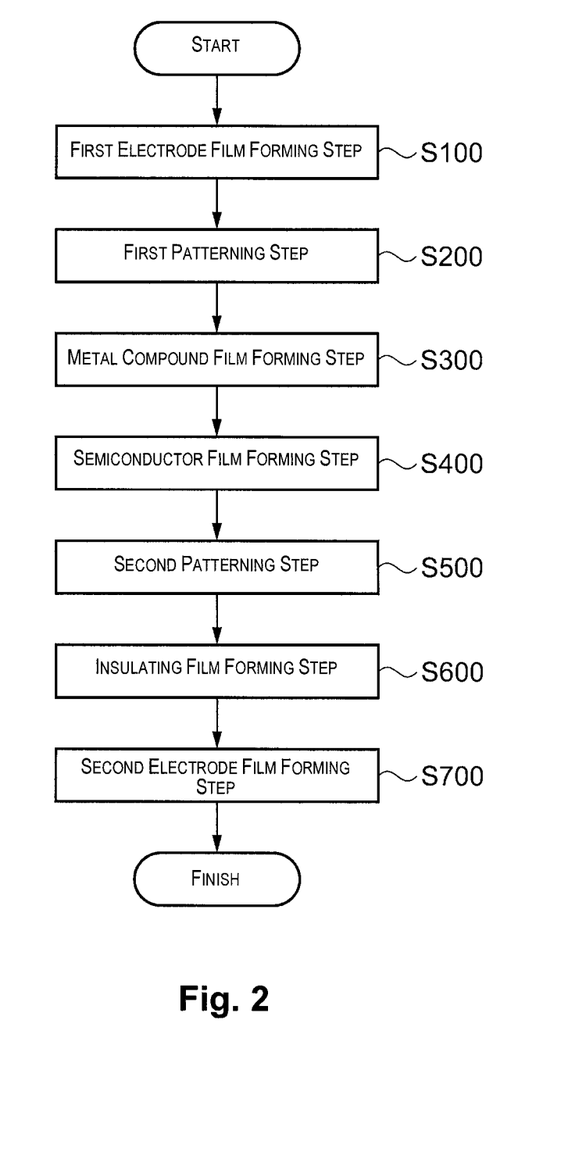
FIG. 2 is a flow chart illustrating steps where the photoelectric conversion element according to the first embodiment is manufactured.
Figure 3A:
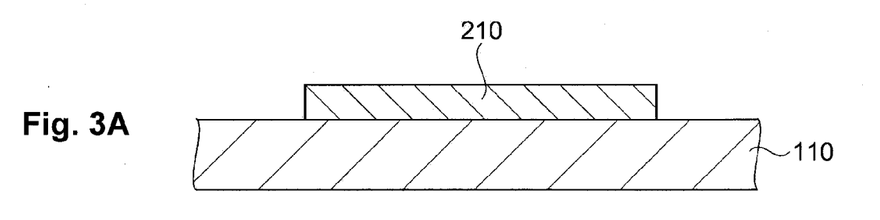
FIGS. 3A, 3B, and 3C are diagrams describing steps where the photoelectric conversion element according to the first embodiment is manufactured.
Figure 3B:
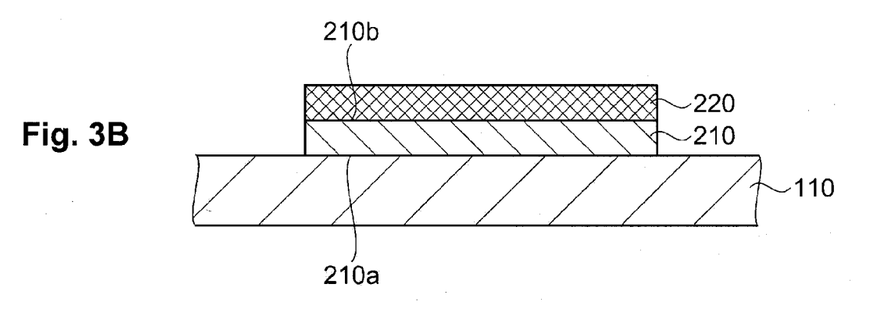
Figure 3C:
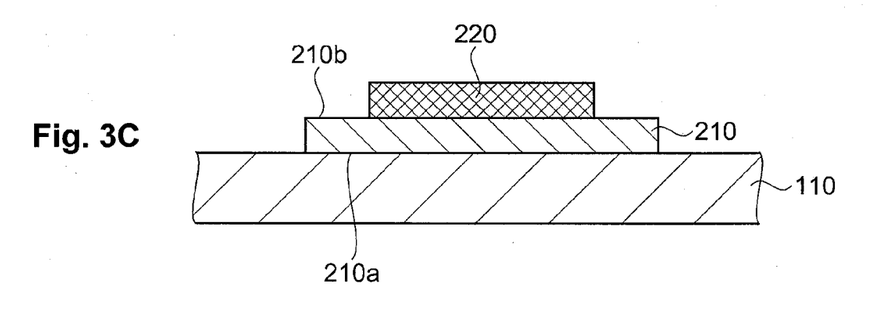
Figure 4A:
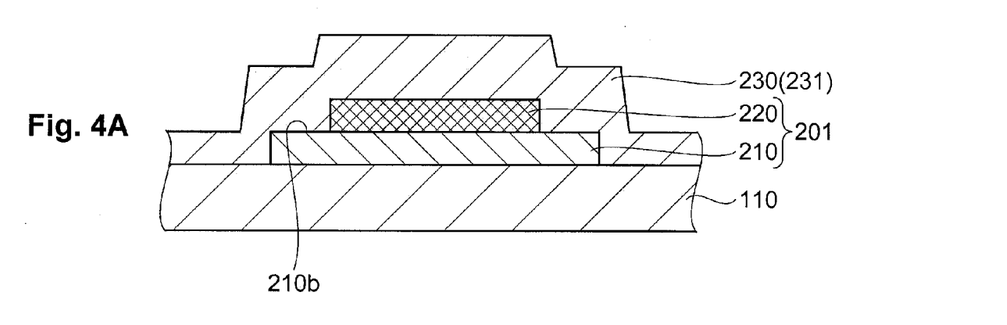
FIGS. 4A, 4B and 4C are diagrams describing steps where the photoelectric conversion element according to the first embodiment is manufactured.
Figure 4B:
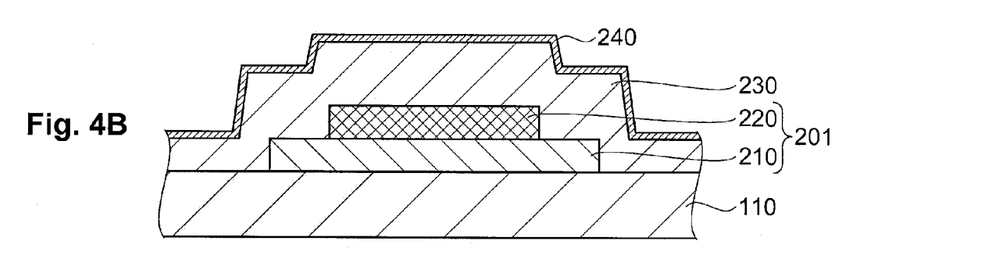
Figure 4C:
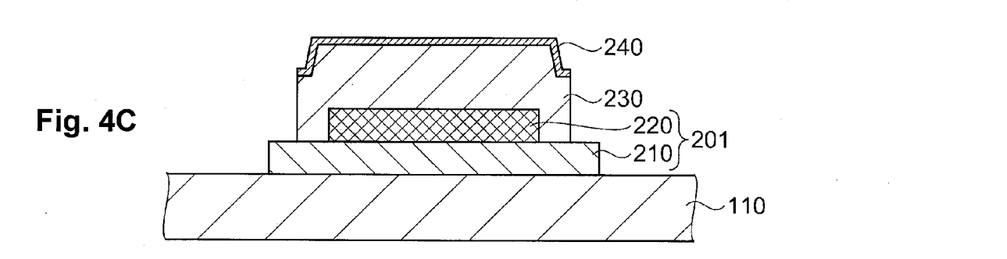
Figure 5A:
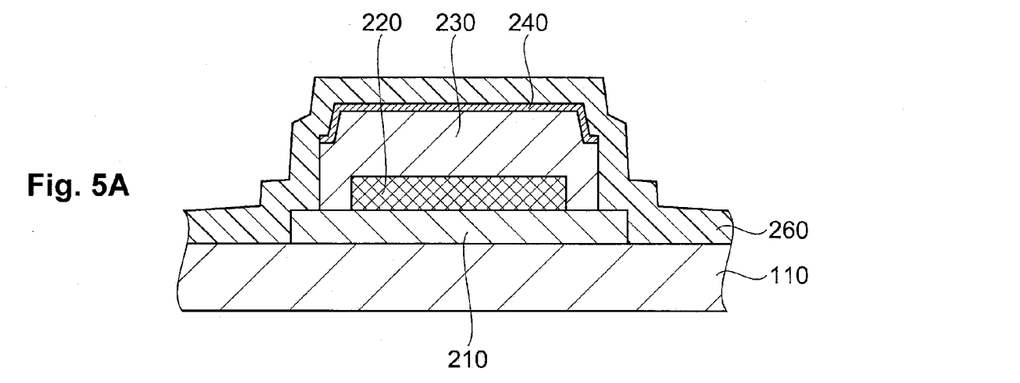
FIGS. 5A, 5B, and 5C are diagrams describing steps where the photoelectric conversion element according to the first embodiment is manufactured.
Figure 5B:
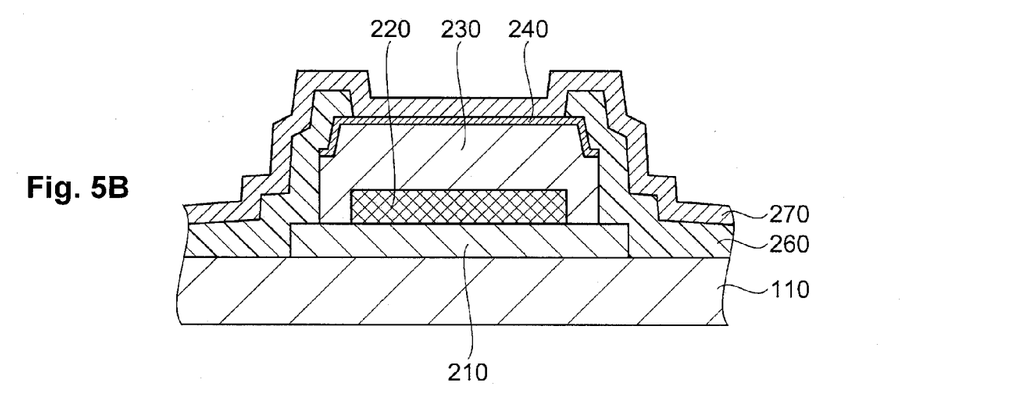
Figure 5C:
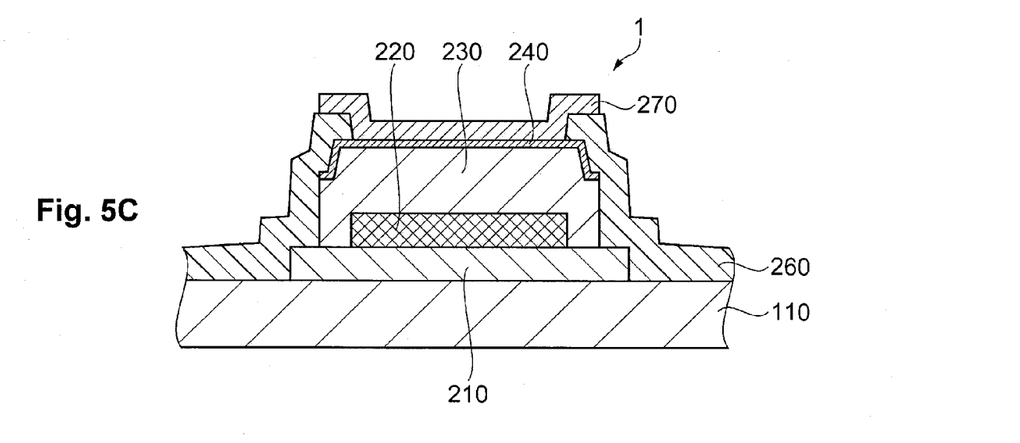

FIGS. 1A and 1B are diagrams illustrating a schematic configuration of the photoelectric conversion element according to the present embodiment. FIG. 2 is a diagram illustrating a flow of steps where the photoelectric conversion element is manufactured. In addition, FIG. 3 to FIG. 5 are diagrams illustrating steps of manufacturing the photoelectric conversion element. Here, the photoelectric conversion element of the present embodiment is, for example, provided in an array shape on a substrate as shown in FIG. 1A and the photoelectric conversion elements shown in each of the diagrams are shown as cross sections where a portion is enlarged.

Structure of Photoelectric Conversion Element

A photoelectric conversion element 1 shown in FIG. 1B is provided with a substrate 110 and a photoelectric conversion section 200. In addition, FIG. 1B illustrates a cross section where the photoelectric conversion element 1 shown in FIG. 1A is enlarged. Here, the same applies to the photoelectric conversion element 1 which is illustrated in FIG. 3 to FIG. 5.

The photoelectric conversion section 200 is configured by a first electrode section 201, a light absorbing section 202, and a second electrode section 203 on the substrate 110 described above.

The first electrode section 201 is provided with a first conductive film 210 and a second conductive film 220 which are provided as a first electrode film. The light absorbing section 202 is provided with a metal compound film 230, a semiconductor film 240, and an insulating film 260. In addition, the second electrode section 203 is provided with a second electrode film 270.

Here, in the following description, the first electrode film will be described using the same reference numeral (201) as the first electrode section.

The photoelectric conversion section 200 of the photoelectric conversion element 1 is provided with a first electrode film 201 on the substrate 110 as shown in FIG. 1B and further provided with the light absorbing section 202 and the second electrode section 203 which overlap with the first electrode film 201.

The substrate 110 is formed to include a material such as glass. For example, borosilicate glass or the like is used as the substrate 110.

Structure of Photoelectric Conversion Section

The first electrode film 201 is provided with the first conductive film 210 on the substrate 110 and the second conductive film 220 on the first conductive film 210.

The first conductive film 210 has a first surface 210a and a second surface 210b with a front and back relationship.

The first conductive film 210 is provided with the first surface 210a connected with the substrate 110 and is patterned into a predetermined shape. The first conductive film 210 is provided as a conductive film which includes titanium (Ti) and the like.

The second conductive film 220 is provided to be patterned in a predetermined shape on the first conductive film 210. In more detail, the second conductive film 220 is provided to be connected with the second surface 210b of the first conductive film 210 and is patterned into the predetermined shape. In addition, the second conductive film 220 is provided at the inner side of the peripheral edge in a case where the first conductive film 210 is seen in a planar view. In other words, the second conductive film 220 has a region with an area which is smaller than the first conductive film 210 where the second conductive film 220 is not provided on the second surface 210b of the first conductive film 210.

Here, the second conductive film 220 is provided as a conductive film which includes molybdenum (Mo) and the like.

Next, the light absorbing section 202 is provided with the metal compound film 230 so as to cover and surround the first electrode film 201. In addition, the semiconductor film 240 is provided on the metal compound film 230. In addition, the insulating film 260 is provided so as to surround the first conductive film 210, the metal compound film 230, and the semiconductor film 240 to correspond to the substrate 110.

The light absorbing section 202 of the present embodiment is a semiconductor device which has a chalcopyrite structure and converts light which is incident on the photoelectric conversion element 1 into an electric (current) signal.

The light absorbing section 202 is provided with the metal compound film 230 as a p type semiconductor which has a chalcopyrite structure which includes a Ib (1b) group element, a IIIb (3b) group element, and a VIb (6b) group element, and an n type semiconductor film 240 to be described later which is connected with the metal compound film 230.

A metal compound film 231 (230) is provided to include copper (Cu), indium (In), and the like. The metal compound film 231 is provided as the metal compound film 230, which is selenized, by performing heating, so-called annealing, in a selenium (Se) atmosphere. The selenized metal compound film 230 described above is a so-called CIS (Cu, In, and Se) thin film.

In addition, it is possible to provide the metal compound film 231 (230) to include copper (Cu), Indium (In), gallium (Ga), and the like. The metal compound film 231 is provided as the selenized metal compound film 230 by performing annealing which is heating in a selenium (Se) atmosphere. The selenized metal compound film 230 described above is a so-called CIGS (Cu, In, Ga, and Se) thin film.

For example, the semiconductor film 240 is provided to include zinc oxide (ZnO) and the like in the n type semiconductor film 240.

The insulating film 260 is provided to cover and surround the first conductive film 210, the metal compound film 230, and the semiconductor film 240 to correspond so as to overlap with the substrate 110.

Here, the insulating film 260 is provided with an exposed region 251 where a portion is opened and the semiconductor film 240 is exposed. In other words, the exposed region 251 is a region where the semiconductor film 240 is not covered by the insulating film 260. For example, the insulating film 260 is provided to include silicon oxide (SiO2).

Next, the second electrode section 203 is an electrode film which extracts the electric (current) signal from the light absorbing section 202. The second electrode film 270 is provided to be patterned into a predetermined shape so as to overlap with the insulating film 260. Here, a portion of the second electrode film 270 is connected with the semiconductor film 240 which is provided in the light absorbing section 202 by the exposed region 251. For example, the second electrode film 270 is formed as a conductive film which includes ITO (indium tin oxide) and the like.

Method of Manufacturing Photoelectric Conversion Element 1

Next, each step in the manufacturing of the photoelectric conversion element 1 will be described.

As shown in FIG. 2, the steps in the manufacturing of the photoelectric conversion element 1 include a first electrode film forming step S100, a first patterning step S200, a metal compound film forming step S300, a semiconductor film forming step S400, a second patterning step S500, an insulating film forming step S600, and a second electrode film forming step S700. Below, the steps in the manufacturing of the photoelectric conversion element 1 will be described in order using FIG. 3 to FIG. 5.

First Electrode Film Forming Step

The first electrode film forming step S100 is a step where the first conductive film 210 and the second conductive film 220 are formed as the first electrode film 201.

The first electrode film forming step S100 includes a step where the first conductive film 210 which includes titanium (Ti) is formed to be connected with the substrate 110, a step where the first conductive film 210 is patterned in the predetermined shape, and a step where the second conductive film 220 which includes molybdenum (Mo) is formed to be connected with the first conductive film 210 which is formed in the predetermined shape.

FIG. 3A illustrates a state where the first conductive film 210 is formed in the predetermined shape on the substrate 110. In addition, FIG. 3B illustrates a state where the second conductive film 220 is formed on the second surface 210b of the first conductive film 210 described above.

For example, in the step where the first conductive film 210 is formed, a conductive film which includes titanium is formed on the substrate 110 using a sputtering method or the like.

For example, in the step where the first conductive film 210 is formed in the predetermined shape, a mask pattern (which is not shown in the diagram) is formed on the second surface 210b of the first conductive film 210 using a photolithography method or the like.

Next, removal (etching) of a portion of the first conductive film 210 which is not necessary is performed using a wet etching method or the like at a region where the mask pattern described above is not formed, that is, the predetermined shape. The removal of the first conductive film 210 in the present embodiment uses a wet etching method where the first conductive film 210 is immersed in an etchant (an aqueous solution) which includes hydrofluoric acid, but the etching method is not limited to this and may be appropriately changed depending on the composition or the like of the first conductive film 210 to be removed.

For example, in the step where the second conductive film 220 is formed, a conductive film which includes molybdenum is formed using a sputtering method or the like on the first conductive film 210 which is formed in the predetermined shape.

First Patterning Step

The first patterning step S200 is a step where the second conductive film 220 is patterned in the predetermined shape.

FIG. 3C illustrates a state where the second conductive film 220 is patterned in the predetermined shape in the first patterning step S200.

For example, in the first patterning step S200, a mask pattern (which is not shown in the diagram) is formed on the second conductive film 220 and the substrate 110 using a photolithography method or the like. Next, removal (etching) of a portion of the second conductive film 220 which is not necessary is performed using a wet etching method or the like at a region where the mask pattern is not formed, that is, the predetermined shape. In the first patterning step S200 in the present embodiment, a wet etching method is used where the second conductive film 220 is immersed in an etchant (an aqueous solution) which includes nitric acid and phosphoric acid.

It is possible to decrease the etching rate with regard to the first conductive film 210 and, on the other hand, to increase the etching rate with regard to the second conductive film 220 by using the etchant which includes nitric acid and phosphoric acid. Due to this, it is possible to selectively etch the second conductive film 220 which includes molybdenum and to suppress corrosion of the first electrode film 201 which includes titanium and the substrate 110. In addition, since the etching rate with regard to the second conductive film 220 is fast, it is possible to suppress corrosion, or so-called site etching, of the side surface of the second conductive film 220. Accordingly, it is possible to suppress residue of the second conductive film 220, which is to be removed in these steps, from occurring on the second surface 210b of the first conductive film 210.

Metal Compound Film Forming Step

The metal compound film forming step S300 is a step where the metal compound film 230 (231) is formed to be connected with the first electrode film 201 and include copper (Cu) and indium (In), or copper (Cu), indium (In), gallium (Ga), and the like.

FIG. 4A illustrates a state where the metal compound film 230 is formed on the first electrode film 201 and the substrate 110 described above in the metal compound film forming step S300.

For example, in the metal compound film forming step S300, the metal compound film 231 (230) which includes copper (Cu) and indium (In), or copper (Cu), indium (In), gallium (Ga), and the like is formed using a sputtering method.

In addition, the metal compound film forming step S300 includes a selenization step where heating of the metal compound film 231, so-called annealing, is performed in a selenium (Se) atmosphere. The metal compound film 231 is formed as a so-called CIS (Cu, In, Se2) thin film or a CIGS (Cu, In, Ga, Se2) thin film which is selenized by annealing in a selenium (Se) atmosphere in the selenization step. In the selenization step in the present embodiment, the annealing temperature is set to approximately 300 □C. Here, the annealing temperature may be appropriately changed depending on the composition of the metal compound film 231.

Semiconductor Film Forming Step

The semiconductor film forming step S400 is a step where the semiconductor film 240 is formed to be connected with the metal compound film 230 which is formed in the metal compound film forming step S300 described above.

FIG. 4B illustrates a state where the semiconductor film 240 is formed on the metal compound film 230 in this step.

For example, in the semiconductor film forming step S400, the n type semiconductor film 240 which includes zinc oxide (ZnO) or the like is formed using a CVD (Chemical Vapor Deposition) method.

Second Patterning Step

The second patterning step S500 is a step where the metal compound film 230 and the semiconductor film 240 are formed in a predetermined shape. FIG. 4F illustrates a state where the metal compound film 230 and the semiconductor film 240 are patterned in the predetermined shape in the second patterning step S500.

For example, in the second patterning step S500, a mask pattern (which is not shown in the diagram) is formed on the semiconductor film 240 using a lithography method and removal (etching) of the semiconductor film 240 and the metal compound film 230 which are not necessary is performed by a wet etching method or the like at a region where a mask pattern is not formed, that is, the predetermined shape.

Insulating Film Forming Step

The insulating film forming step S600 is a step where the insulating film 260 is formed so as to surround the first conductive film 210, the metal compound film 230, and the semiconductor film 240 to correspond so as to overlap with the substrate 110.

FIG. 5A illustrates a state where the insulating film 260 is formed in this step.

For example, in the insulating film forming step S600, the insulating film 260 which includes silicon nitride (SiNx) or silicon oxide (SiO2) is formed using a chemical vapor deposition method. By including silicon oxide in the insulating film 260, the adhesion between the substrate 110, the metal compound film 230, the semiconductor film 240, and the second electrode film 270 is increased and it is possible to suppress the peeling between each of these and the insulating film 260.

Second Electrode Film Forming Step

The second electrode film forming step S700 is a step where the second electrode film 270 is formed to be connected with the semiconductor film 240 described above on the insulating film 260.

The second electrode film forming step S700 includes a step where the second electrode film 270 is formed and a step where the exposed region 251 which connects the second electrode film 270 and the semiconductor film 240 is formed. FIG. 5B illustrates a state where the second electrode film 270 is formed to be connected with the semiconductor film 240 in this step.

In addition, the second electrode film forming step S700 includes a step where the second electrode film 270 which is formed is patterned in a predetermined shape. FIG. 5C illustrates a state where the second electrode film 270 is patterned in the predetermined shape by this step.

In the second electrode film forming step S700, forming of the exposed region 251 is performed prior to forming of the second electrode film 270. For example, in the step where the exposed region 251 is formed, a mask pattern (which is not shown in the diagram) where a portion which is the exposed region 251 is opened is formed on the second electrode film 270 using a photolithography method. Next, removal (etching) of the insulating film 260, which is formed in a portion where the mask pattern is opened, that is, a portion which is the exposed region 251, is performed using a dry etching method or the like. Etching gas which includes sulfur hexafluoride (SF6) is used in the dry etching of the present embodiment but the dry etching is not limited to this and the etching gas may be appropriately changed according to the composition and the like of the insulating film 260.

Next, in the second electrode film forming step S700, forming of the second electrode film 270 is performed so that the second electrode film 270 is connected with the semiconductor film 240. In the forming of the second electrode film 270, for example, the second electrode film 270 which includes ITO is formed on the insulating film 260 and on the semiconductor film 240 which is exposed in the exposed region 251 using a sputtering method.

Next, in the second electrode film forming step S700, a step is performed where patterning of the second electrode film 270 is performed in the predetermined shape. In the patterning of the second electrode film 270, for example, on the second electrode film 270 which is formed, a mask pattern (which is not shown in the diagram) is formed on the insulating film 260 using a photolithography method and removal (etching) of the second electrode film 270 which is not necessary is performed using a wet etching method or the like at a region where a mask pattern is not formed, that is, the predetermined shape.

In the second electrode film forming step S700 in the present embodiment, a wet etching method where the second electrode film 270 is immersed into an etchant (an aqueous solution) which includes oxalic acid is used but the etching method is not limited to this and may be appropriately changed depending on the composition or the like of the second electrode film 270 or the like.

When the second electrode film forming step S700 is completed, the steps in the manufacturing of the photoelectric conversion element 1 are completed.

According to the first embodiment described above, the following effects are obtained.

According to the photoelectric conversion element 1, by performing the first patterning step S200 where the second conductive film 220 which is formed on the first conductive film 210 is formed in the predetermined shape prior to the metal compound film forming step S300 where the metal compound film 230 is formed, the second conductive film 220 is provided on the first conductive film 210 so as to surround the first conductive film 210 and the metal compound film 230.

Due to this, it is possible to selectively remove unnecessary portions of the second conductive film 220 which is patterned on the first conductive film 210 using wet etching and it is possible to suppress residue from the etched second conductive film from occurring +++ on the first conductive film 210 and corrosion of the first conductive film 210 and the substrate 110.

Accordingly, it is possible to obtain the photoelectric conversion element 1 with a high SN ratio where current which leaks out from the second conductive film 220, that is, dark current, is suppressed.

Second Embodiment

Figure 6:
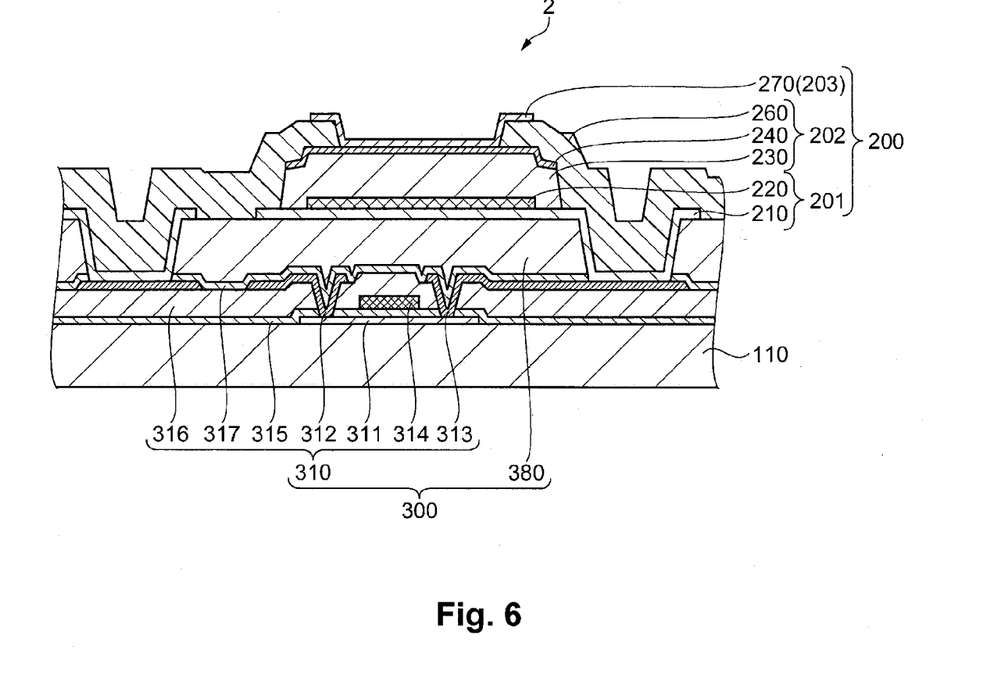
FIG. 6 is a diagram schematically illustrating a schematic configuration of a photoelectric conversion element according to a second embodiment.

FIG. 6 is a diagram schematically illustrating a schematic configuration of a photoelectric conversion element according to the present embodiment.

A photoelectric conversion element 2 of the present embodiment is the photoelectric conversion element 1 which was described in the first embodiment which is provided with a circuit section 300.

Structure of Photoelectric Conversion Element 2

The photoelectric conversion element 2 shown in FIG. 6 is provided with the substrate 110, the circuit section 300, and the photoelectric conversion section 200.

The circuit section 300 is provided with a switching element 310 on the substrate 110. In addition, the circuit section 300 is provided with a planarization film 320 which covers the switching element 310.

The photoelectric conversion section 200 is provided with the first electrode section 201, the light absorbing section 202, and the second electrode section 203 on the planarization film 320 described above.

The photoelectric conversion element 2 is provided on the substrate 110 as shown in FIG. 6 to overlap with the circuit section 300 and the photoelectric conversion section 200.

Structure of Circuit Section

In the circuit section 300, the switching element 310 is provided on the substrate 110 as a thin film transistor which is configured by a switching semiconductor section 311, a source electrode 312, a drain electrode 313, a gate electrode section 314, a gate insulating section 315, an interlayer insulating section 316, and a protective section 317. In the present embodiment, as the switching element 310, a so-called polysilicon thin film transistor where polycrystalline silicon is used in the switching semiconductor section 311 is exemplified. However, the switching element 310 is not limited to this and an amorphous silicon thin film transistor or a transistor which uses another semiconductor film may be provided.

In addition, the planarization film 320 is provided in the circuit section 300 so as to cover the switching element 310. For example, the planarization film 320 is provided to include silicon oxide ($SiO_2$).

Structure of Photoelectric Conversion Section

The photoelectric conversion section 200 is provided with the first electrode section 201, the light absorbing section 202, and the second electrode section 203 overlapping in the same manner as the first embodiment. In the photoelectric conversion section 200, the first conductive film 210 and the drain electrode 313 which is provided on the circuit section 300 are connected. Other than this, since the structure of the photoelectric conversion section 200 is the same as the photoelectric conversion element 1 which was described in the first embodiment, description of the structure will be omitted.

Method of Manufacturing Photoelectric Conversion Element 2

Next, the steps of manufacturing the photoelectric conversion element 2 will be described.

In the method of manufacturing the photoelectric conversion element 2, the step where the switching element 310 is formed is performed prior to the step where the photoelectric conversion section 200 of the photoelectric conversion element 1 which was described in the first embodiment is manufactured.

In the step where the switching element 310 in the present embodiment is formed, it is possible to use polysilicon thin film transistor manufacturing techniques which are well-known techniques. Here, for example, in the forming of the planarization film 320 which covers the switching element 310, it is possible to form a film which includes silicon oxide ($SiO_2$) or the like using the chemical vapor deposition method.

Other than this, since the step where the photoelectric conversion element 2 is manufactured is the same as the step where the photoelectric conversion element 1 which was described in the first embodiment is manufactured, description of the step will be omitted.

According to the second embodiment described above, the following effects are obtained.

According to the photoelectric conversion element 2, by operating the switching element 310 according to the electric signal which is converted by the photoelectric conversion section 200, for example, it is possible to easily detect the portion where light is incident to the photoelectric conversion element 2 in a case (refer to FIG. 1A) where the photoelectric conversion element 2 is provided in an array shape.

EXAMPLE

Next, based on FIG. 7, an example of the electronic device will be described where the photoelectric conversion element 1 according to one embodiment of the present invention is applied.

Electronic Device

Figure 7:
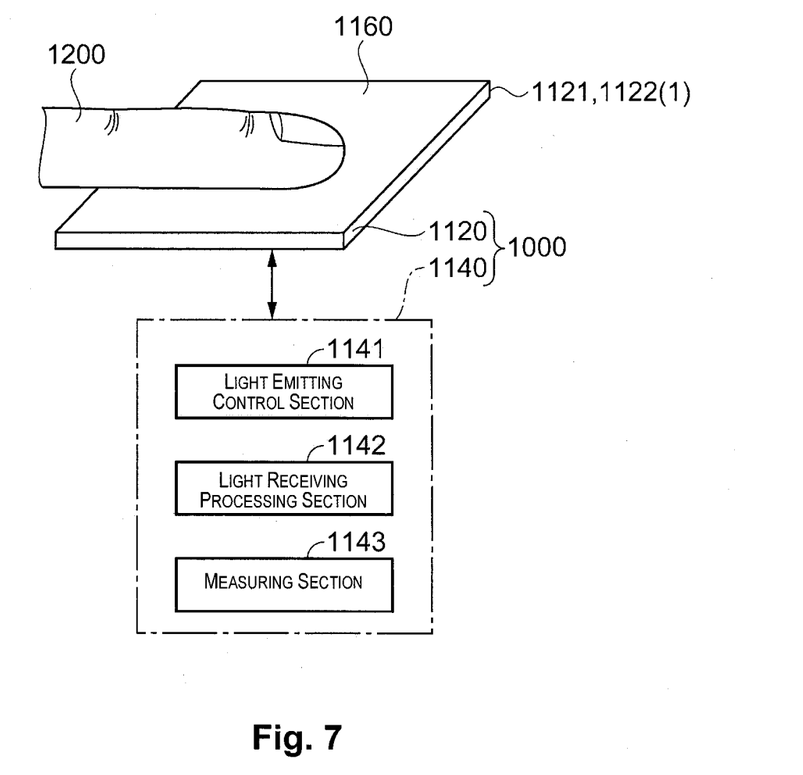
FIG. 7 is a diagram schematically illustrating an electronic device according to an example.

FIG. 7 is a diagram illustrating an outline of an alcohol concentration measuring apparatus 1000 as an electronic device which is provided with the photoelectric conversion element 1 according to an embodiment of the present invention. The alcohol concentration measuring apparatus 1000 shown in FIG. 7 is an apparatus which measures the alcohol concentration in blood by irradiating light onto the blood which is flowing through veins and receiving the light which is reflected with the photoelectric conversion element 1.

The alcohol concentration measuring apparatus 1000 is provided with an imaging apparatus 1120 which irradiates light onto a finger 1200 and receives the light which is reflected, and a control apparatus 1140.

The imaging apparatus 1120 is provided with a light emitting section 1121 and the photoelectric conversion element 1 as a light receiving section 1122. In addition, the imaging apparatus 1120 is provided with a detection surface 1160 where the finger 1200 is placed.

The control apparatus 1140 is provided with a light emitting control section 1141 which controls the light emitting section 1121, a light receiving processing section 1142 which processes the electric signal which is output from the photoelectric conversion element 1 as the light receiving section 1122, and a measuring section 1143 which measures the alcohol concentration based on the signal which was processed by the light receiving processing section 1142.

For the alcohol concentration measuring apparatus 1000 as the electronic device which is provided with the photoelectric conversion element 1, it is possible to increase the light receiving sensitivity of the light which is reflected from the blood by mounting the photoelectric conversion element 1 according to the embodiments of the present invention as the light receiving section 1122.

Here, it is possible for the photoelectric conversion element 1 according to an embodiment of the present invention to be applied to, for example, a biometric authentication apparatus, a fingerprint imaging apparatus, a vein pattern imaging apparatus, a solar battery apparatus, and the like in addition to the alcohol concentration measuring apparatus 1000 in FIG. 7.

General Interpretation of Terms

In understanding the scope of the present invention, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" or "element" when used in the singular can have the dual meaning of a single part or a plurality of parts. Finally, terms of degree such as "substantially", "about" and "approximately" as used herein mean a reasonable amount of deviation of the modified term such that the end result is not significantly changed. For example, these terms can be construed as including a deviation of at least ±5% of the modified term if this deviation would not negate the meaning of the word it modifies.

While only selected embodiments have been chosen to illustrate the present invention, it will be apparent to those skilled in the art from this disclosure that various changes and modifications can be made herein without departing from the scope of the invention as defined in the appended claims. Furthermore, the foregoing descriptions of the embodiments according to the present invention are provided for illustration only, and not for the purpose of limiting the invention as defined by the appended claims and their equivalents.

What is claimed is:

1. A photoelectric conversion element comprising:
   a substrate; and
   a photoelectric conversion section having a first electrode section and a second electrode section which are provided on the substrate, and a light absorbing section,
   wherein the first electrode section has
      a first conductive film having a first surface and a second surface, which is in a front and back relationship with the first surface, with the first surface of the first conductive film being connected with the substrate, and
      a second conductive film connected with the second surface of the first conductive film and provided at an inner side of a peripheral edge of the first conductive film,
   the light absorbing section has
      a metal compound film covering the second conductive film and connected with the second surface of the first conductive film,
      a semiconductor film connected with the metal compound film, and
      an insulating film connected with the substrate with the insulating film surrounding the first conductive film, the metal compound film, and the semiconductor film, and exposing the semiconductor film by a portion of the insulating film being opened, and
   the second electrode section has a second electrode film which is provided on the insulating film and connected with the semiconductor film which is exposed from the insulating film.

2. The photoelectric conversion element according to claim 1, wherein
   the metal compound film includes copper (Cu), indium (In), and selenium (Se).

3. The photoelectric conversion element according to claim 1, wherein
   the insulating film includes silicon oxide.

4. An electronic device including the photoelectric conversion element according to claim 1.

* * * * *